US009999359B2

(12) United States Patent
Thakur et al.

(10) Patent No.: US 9,999,359 B2
(45) Date of Patent: Jun. 19, 2018

(54) SYSTEM AND METHODS FOR DETECTING ATRIAL TACHYARRHYTHMIA USING HEMODYNAMIC SENSORS

(71) Applicant: Cardiac Pacemakers, Inc., St. Paul, MN (US)

(72) Inventors: Pramodsingh Hirasingh Thakur, Woodbury, MN (US); Qi An, Blaine, MN (US); Barun Maskara, Blaine, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 106 days.

(21) Appl. No.: 14/698,007

(22) Filed: Apr. 28, 2015

(65) Prior Publication Data
US 2015/0342466 A1 Dec. 3, 2015

Related U.S. Application Data

(60) Provisional application No. 62/004,481, filed on May 29, 2014.

(51) Int. Cl.
*A61B 5/024* (2006.01)
*A61N 1/39* (2006.01)
(Continued)

(52) U.S. Cl.
CPC .............. *A61B 5/024* (2013.01); *A61B 5/0205* (2013.01); *A61B 5/046* (2013.01); *A61B 5/7282* (2013.01);
(Continued)

(58) Field of Classification Search
CPC .............. A61N 1/36585; A61N 1/3622; A61N 1/3624; A61N 1/36507; A61N 1/36514;
(Continued)

(56) References Cited

U.S. PATENT DOCUMENTS 6,491,639 B1 12/2002 Turcott
7,853,327 B2 12/2010 Patangay et al.
(Continued)

OTHER PUBLICATIONS

U.S. Appl. No. 14/717,342, filed May 20, 2015, Method and Apparatus for Detecting Atrial Tachyarrhythmia Using Heart Sounds.
(Continued)

*Primary Examiner* — Mark W Bockelman
(74) *Attorney, Agent, or Firm* — Schwegman Lundberg & Woessner, P.A.

(57) ABSTRACT

Systems and methods for detecting atrial tachyarrhythmias such as atrial fibrillation (AF) are disclosed. A medical system can sense a heart rate (HR) output and a hemodynamic status output. An AF detector circuit automatically determines a first detection criterion and a different second detection criterion. The first detection criterion can be more sensitive to the presence of the AF episode than the second detection criterion, and the second detection criterion can be more specific to the AF episode than the first detection criterion. The AF detector circuit detects an AF onset event using the first detection criterion and at least one of the heart rate output or the hemodynamic status output, and detects an AF termination event using the second detection criterion and at least one of the heart rate output or the hemodynamic status output.

20 Claims, 7 Drawing Sheets

(51) Int. Cl.
*A61B 5/046* (2006.01)
*A61B 7/02* (2006.01)
*A61B 5/0205* (2006.01)
*A61N 1/362* (2006.01)
*A61B 5/11* (2006.01)
*A61B 5/08* (2006.01)
*A61B 5/00* (2006.01)
*A61B 5/0215* (2006.01)
*A61B 5/0245* (2006.01)
*A61B 5/042* (2006.01)
*A61B 5/0452* (2006.01)
*A61B 5/0456* (2006.01)
*A61B 5/053* (2006.01)
*A61B 5/1455* (2006.01)
*A61B 5/1459* (2006.01)
*A61N 1/365* (2006.01)

(52) U.S. Cl.
CPC ............ *A61B 7/023* (2013.01); *A61N 1/3622* (2013.01); *A61N 1/3624* (2013.01); *A61N 1/36585* (2013.01); *A61B 5/0215* (2013.01); *A61B 5/0245* (2013.01); *A61B 5/02405* (2013.01); *A61B 5/042* (2013.01); *A61B 5/0452* (2013.01); *A61B 5/0456* (2013.01); *A61B 5/0538* (2013.01); *A61B 5/0809* (2013.01); *A61B 5/1102* (2013.01); *A61B 5/1118* (2013.01); *A61B 5/1459* (2013.01); *A61B 5/14551* (2013.01); *A61B 5/686* (2013.01); *A61B 5/6869* (2013.01); *A61B 2562/0204* (2013.01); *A61B 2562/0219* (2013.01); *A61N 1/36507* (2013.01); *A61N 1/36514* (2013.01)

(58) Field of Classification Search
CPC ......... A61B 7/023; A61B 5/046; A61B 5/686; A61B 5/024; A61B 5/0205; A61B 5/7282; A61B 5/6869; A61B 2562/0204; A61B 2562/0219; A61B 5/1459; A61B 5/0215; A61B 5/0245; A61B 5/042; 5/0452; A61B 5/0456; A61B 5/0538; A61B 5/1102; A61B 5/14551; A61B 5/1118; A61B 5/0809; A61B 5/02405
See application file for complete search history.

(56) References Cited

U.S. PATENT DOCUMENTS

| | | |
|---|---|---|
| 2004/0230129 A1 | 11/2004 | Haefner |
| 2007/0149890 A1 | 6/2007 | Li et al. |
| 2009/0043218 A1 | 2/2009 | Warner et al. |
| 2010/0198285 A1 | 8/2010 | Rom |
| 2010/0241180 A1 | 9/2010 | Whitman et al. |
| 2010/0331903 A1 | 12/2010 | Zhang et al. |
| 2011/0224555 A1 | 9/2011 | Park |
| 2013/0237872 A1 | 9/2013 | Zhang et al. |

OTHER PUBLICATIONS

"U.S. Appl. No. 14/717,342, Non Final Office Action dated Jun. 2, 2017", 8 pgs.

"U.S. Appl. No. 14/717,342, Non Final Office Action dated Nov. 27, 2017", 8 pgs.

"U.S. Appl. No. 14/717,342, Response filed Jul. 17, 2017 to Non Final Office Action dated Jun. 2, 2017", 12 pgs.

SYSTEM AND METHODS FOR DETECTING ATRIAL TACHYARRHYTHMIA USING HEMODYNAMIC SENSORS

CLAIM OF PRIORITY

This application claims the benefit of priority under 35 U.S.C. § 119(e) of U.S. Provisional Patent Application Ser. No. 62/004,481, filed on May 29, 2014, which is herein incorporated by reference in its entirety.

TECHNICAL FIELD

This document relates generally to medical devices, and more particularly, to systems, devices and methods for detecting atrial tachyarrhythmia using hemodynamic sensors.

BACKGROUND

Atrial fibrillation (AF) is the most common clinical arrhythmia, and accounts for approximately one third of admissions resulting from cardiac rhythm disturbances. An estimated 2.3 million people in North America have AF. During AF, the normal regular sinus rhythm is overwhelmed by disorganized electrical pulses originated from regions in or near an atrium. This can lead to irregular conductions to ventricles, thereby causing inappropriately fast and irregular heart rate. One type of AF is paroxysmal AF which may last from minutes to days before it stops by itself. Another type known as persistent AF may last for over a week and typically requires medication or other treatment to revert to normal sinus rhythm. The third type, permanent AF, is a condition where a normal heart rhythm cannot be restored with treatment. Persistent AF can become more frequent and result in permanent AF.

Congestive heart failure (CHF) is another major cardiovascular epidemic and affects over five million people in the United States alone. CHF is the loss of pumping power of the heart, resulting in the inability to deliver enough blood to meet the demands of peripheral tissues. CHF patients typically have enlarged heart with weakened cardiac muscles, resulting in reduced contractility and poor cardiac output of blood. CHF can affect the left heart, right heart or both sides of the heart, resulting in non-simultaneous contractions of the left ventricle and contractions of the right ventricle. Such non-simultaneous contractions, also known as dyssynchrony between the left and right ventricles, can further decrease the pumping efficiency of the heart.

There is a close pathophysiological relationship between AF and CHF. A large percentage of CHF patients may experience AF or other types of atrial tachyarrhythmias. AF may facilitate the development or progression of CHF, and CHF can increase the risk for the development of AF. The prevalence of AF in patients with CHF increased in parallel with the severity of CHF.

OVERVIEW

Atrial tachyarrhythmias, such as AF, can coexist with HF in many CHF patients. AF may facilitate the development or progression of CHF in several ways. For example, during AF, irregularity of the ventricular contractions can result in reduction in left ventricular (LV) filling during short cycles which is not completely compensated for by increased filling during longer cycles. The loss of effective atrial contractile function also contributes to the deterioration of LV filling, particularly in CHF patients with diastolic dysfunction. Presence of untreated or uncontrolled AF may also reduce effectiveness of CHF therapies.

Timely and reliable detection of AF is necessary for treatment of AF and prevention of its exacerbating effect on CHF. Patients with AF frequently experience inappropriately rapid heart rate and irregular ventricular rhythm due to the loss of normal AV synchrony. As such, detection of an AF episode can be usually based on the fast atrial rate, or irregular ventricular contractions. However, atrial activity signal such as P wave in an electrocardiogram (ECG) can be a relatively weak signal compared to ventricular activity such as R wave or QRS complex which is produced by ventricular depolarization. Atrial activity signals can also be contaminated by noise, or interfered by various physiologic or environmental conditions. Although a dedicated atrial sensing such as by using an implanted lead placed in or near the atrium can improve atrial signal quality, it is not applicable to patient not indicated for atrial lead implantation. On the other hand, AF detection based on irregular ventricular contractions may suffer from confounding factors such as ventricular ectopic contracts or improper sensing of ventricular contractions, which may also manifest irregularity in R waves or QRS complexes. This can lead to reduced reliability of the detected ventricular contraction variability and false positive or false negative detections of AF. Therefore, the present inventors have recognized that there remains a considerable need of systems and methods that can reliably and accurately detect an AF episode.

Ambulatory medical devices (AMDs) can be used for monitoring HF patient and detecting HF worsening events. Examples of such ambulatory medical devices can include implantable medical devices (IMDs), subcutaneous medical devices, wearable medical devices or other external medical devices. The ambulatory or implantable medical devices can include physiologic sensors which can be configured to sense electrical activity and mechanical function of the heart, or physical or physiological variables associated with the signs and symptoms of worsening of HF. The medical device can optionally deliver therapy such as electrical stimulation pulses to a target area, such as to restore or improve the cardiac function or neural function.

Some AMDs can include a physiologic sensor that provides diagnostic features. In an example, an AMD can include an impedance sensor to sense the fluid status in the lungs. In another example, an AMD can include sensors for detecting heart sounds. Heart sounds are associated with mechanical vibrations from activity of a patient's heart and the flow of blood through the heart, thus are indicative of a patient's hemodynamic status. Heart sounds recur with each cardiac cycle and are separated and classified according to the activity associated with the vibration. The first heart sound (S1) is associated with the vibrational sound made by the heart during tensing of the mitral valve. The second heart sound (S2) marks the beginning of diastole. The third heart sound (S3) and fourth heart sound (S4) are related to filling pressures of the left ventricle during diastole.

The diagnostic feature provided by the physiologic sensors can indicate a patient's hemodynamic status. For example, heart sounds are useful indicators of proper or improper functioning of a patient's heart, and can be used to assess a patient's hemodynamic status. On the other hand, in patient developing an AF episode, the loss of normal AV synchrony and irregular ventricular rhythm can adversely impact the hemodynamic stability in the patient. The loss of effective atrial contraction may result in a marked decrease in cardiac output, especially for persons with impaired diastolic filling of the ventricles. An ongoing AF can cause more significant hemodynamic deterioration in patients with mitral stenosis, restrictive or hypertrophic cardiomyopathy, pericardial diseases, or ventricular hypertrophy. Therefore, physiologic sensors such as heart sounds sensors can be used to detect AF such as by assessing adverse hemodynamic impact of the AF episode.

Various embodiments described herein can help improve detection of an atrial tachyarrhythmia such as an AF episode, or improve the process of identifying patients at elevated risk of developing an AF episode. For example, a system can comprise a heart rate (HR) sensor circuit that can sense a HR output indicative of a HR of a patient, a hemodynamic sensor circuit configured to sense a hemodynamic status output different from the heart rate output and indicative of a hemodynamic status of the patient, and an AF detector circuit. The AF detector circuit can include a detection criterion determination circuit that determines or receives a first detection criterion and a different second detection criterion. The AF detector circuit can include an AF onset event detector and an AF termination event detector. The AF onset detector can detect an AF onset event indicative of a beginning of an AF episode using the first detection criterion and at least one of the heart rate output or the hemodynamic status output. The AF termination detector can detect an AF termination event indicative of an end of the AF episode using the second detection criterion and at least one of the heart rate output or the hemodynamic status output. The first detection criterion is more sensitive to the presence of the AF episode event than the second criterion, and the second detection criterion is more specific to the presence of the AF episode than the first detection criterion.

In another system embodiment, the system as discussed above can further include an activity sensor circuit configured to sense physical activity or exertion level output of the patient. The detection criterion determination circuit can also determine a first activity or exertion level criterion and a different second activity or exertion criterion. The AF onset event detector can detect an AF onset event when the heart rate output meets a first heart rate criterion, the hemodynamic status output meets a first hemodynamic status criterion, and the sensed activity or exertion level output meets a first activity or exertion criterion. The AF termination event detector can detect the AF termination event when the heart rate output meets a second heart rate criterion, the hemodynamic status output meets a second hemodynamic status criterion, and the sensed activity or exertion level output meets a second activity or exertion criterion.

A method can include processes of receiving from a patient at least a heart rate (HR) parameter and a hemodynamic status parameter different from the HR parameter, and determining or receiving a first detection criterion and a different second detection criterion. The method can include detecting an AF onset event indicative of a beginning of an AF episode using the first detection criterion and at least one of the heart rate output or the hemodynamic status output. In response to the detection of the AF onset, an AF termination event indicative of an end of the AF episode can be detected using the second detection criterion and at least one of the heart rate output or the hemodynamic status output. The first detection criterion is more sensitive to the AF episode than the second detection criterion, and the second detection criterion is more specific to the AF episode than the first detection criterion.

This Overview is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Disclosed herein are systems, devices, and methods for detecting atrial tachyarrhythmias such as atrial fibrillation (AF). By monitoring a patient's hemodynamic status using a hemodynamic sensor such as a heart sound sensor, the system and methods discussed in the present document can be used to timely and reliably detect onset and termination of an AF episode, thereby allowing immediate medical attention to the patient. The systems and methods discussed in this document can also be used for detecting other types of atrial tachyarrhythmias such atrial tachycardia, atrial flutter, or supraventricular tachycardia.

Figure 1:
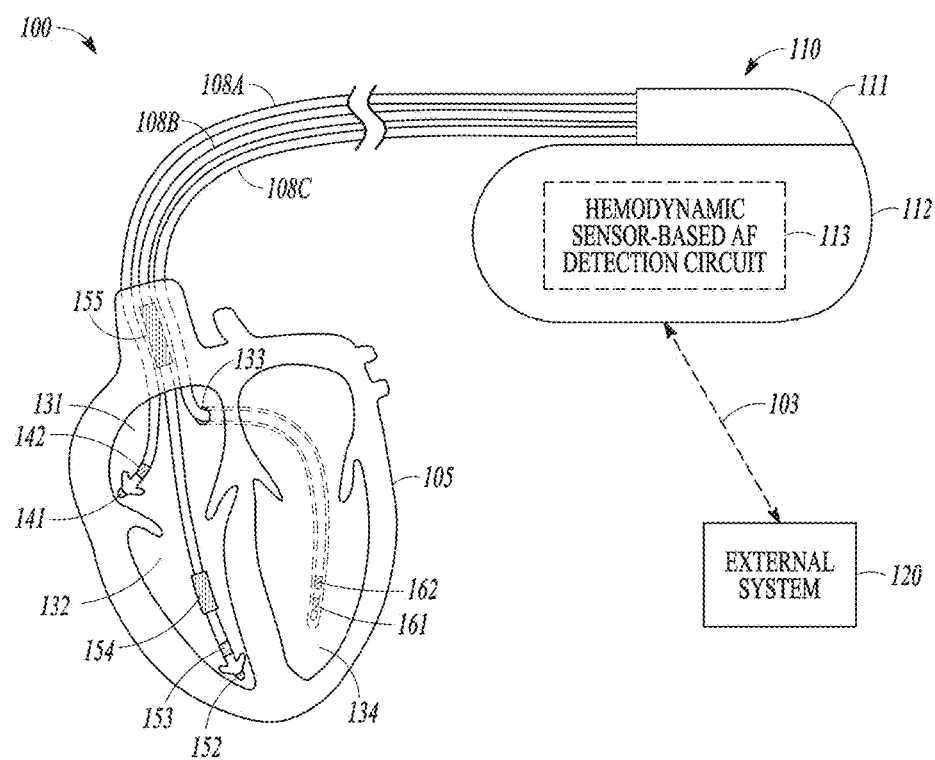
FIG. 1 illustrates an example of a cardiac rhythm management (CRM) system and portions of the environment in which the CRM system operates.

FIG. 1 illustrates an example of a Cardiac Rhythm Management (CRM) system 100 and portions of an environment in which the CRM system 100 can operate. The CRM system 100 can include an ambulatory medical device, such as an implantable medical device (IMD) 110 that can be electrically coupled to a heart 105 such as through one or more leads 108A-C, and an external system 120 that can communicate with the IMD 110 such as via a communication link 103. The IMD 110 may include an implantable cardiac device such as a pacemaker, an implantable cardioverter-defibrillator (ICD), or a cardiac resynchronization therapy defibrillator (CRT-D). The IMD 110 can include one or more monitoring or therapeutic devices such as a subcutaneously implanted device, a wearable external device, a neural stimulator, a drug delivery device, a biological therapy device, a diagnostic device, or one or more other ambulatory medical devices. The IMD 110 may be coupled to, or may be substituted by a monitoring medical device such as a bedside or other external monitor.

As illustrated in FIG. 1, the IMD 110 can include a hermetically sealed can 112 that can house an electronic circuit that can sense a physiological signal in the heart 105 and can deliver one or more therapeutic electrical pulses to a target region, such as in the heart, such as through one or more leads 108A-C. The CRM system 100 can include only one lead such as 108B, or can include two leads such as 108A and 108B.

The lead 108A can include a proximal end that can be configured to be connected to IMD 110 and a distal end that can be configured to be placed at a target location such as in the right atrium (RA) 131 of the heart 105. The lead 108A can have a first pacing-sensing electrode 141 that can be located at or near its distal end, and a second pacing-sensing electrode 142 that can be located at or near the electrode 141. The electrodes 141 and 142 can be electrically connected to the IMD 110 such as via separate conductors in the lead 108A, such as to allow for sensing of the right atrial activity and optional delivery of atrial pacing pulses. The lead 108B can be a defibrillation lead that can include a proximal end that can be connected to IMD 110 and a distal end that can be placed at a target location such as in the right ventricle (RV) 132 of heart 105. The lead 108B can have a first pacing-sensing electrode 152 that can be located at distal end, a second pacing-sensing electrode 153 that can be located near the electrode 152, a first defibrillation coil electrode 154 that can be located near the electrode 153, and a second defibrillation coil electrode 155 that can be located at a distance from the distal end such as for superior vena cava (SVC) placement. The electrodes 152 through 155 can be electrically connected to the IMD 110 such as via separate conductors in the lead 108B. The electrodes 152 and 153 can allow for sensing of a ventricular electrogram and can optionally allow delivery of one or more ventricular pacing pulses, and electrodes 154 and 155 can allow for delivery of one or more ventricular cardioversion/defibrillation pulses. In an example, the lead 108B can include only three electrodes 152, 154 and 155. The electrodes 152 and 154 can be used for sensing or delivery of one or more ventricular pacing pulses, and the electrodes 154 and 155 can be used for delivery of one or more ventricular cardioversion or defibrillation pulses. The lead 108C can include a proximal end that can be connected to the IMD 110 and a distal end that can be configured to be placed at a target location such as in a left ventricle (LV) 134 of the heart 105. The lead 108C may be implanted through the coronary sinus 133 and may be placed in a coronary vein over the LV such as to allow for delivery of one or more pacing pulses to the LV. The lead 108C can include an electrode 161 that can be located at a distal end of the lead 108C and another electrode 162 that can be located near the electrode 161. The electrodes 161 and 162 can be electrically connected to the IMD 110 such as via separate conductors in the lead 108C such as to allow for sensing of the LV electrogram and optionally allow delivery of one or more resynchronization pacing pulses from the LV.

The IMD 110 can include an electronic circuit that can sense a physiological signal. The physiological signal can include an electrogram or a signal representing mechanical function of the heart 105. The hermetically sealed can 112 may function as an electrode such as for sensing or pulse delivery. For example, an electrode from one or more of the leads 108A-C may be used together with the can 112 such as for unipolar sensing of an electrogram or for delivering one or more pacing pulses. A defibrillation electrode from the lead 108B may be used together with the can 112 such as for delivering one or more cardioversion/defibrillation pulses. In an example, the IMD 110 can sense impedance such as between electrodes located on one or more of the leads 108A-C or the can 112. The IMD 110 can be configured to inject current between a pair of electrodes, sense the resultant voltage between the same or different pair of electrodes, and determine impedance using Ohm's Law. The impedance can be sensed in a bipolar configuration in which the same pair of electrodes can be used for injecting current and sensing voltage, a tripolar configuration in which the pair of electrodes for current injection and the pair of electrodes for voltage sensing can share a common electrode, or tetrapolar configuration in which the electrodes used for current injection can be distinct from the electrodes used for voltage sensing. In an example, the IMD 110 can be configured to inject current between an electrode on the RV lead 108B and the can housing 112, and to sense the resultant voltage between the same electrodes or between a different electrode on the RV lead 108B and the can housing 112. A physiologic signal can be sensed from one or more physiological sensors that can be integrated within the IMD 110. The IMD 110 can also be configured to sense a physiological signal from one or more external physiologic sensors or one or more external electrodes that can be coupled to the IMD 110. Examples of the physiological signal can include one or more of electrocardiogram, intracardiac electrogram, arrhythmia, heart rate, heart rate variability, intrathoracic impedance, intracardiac impedance, arterial pressure, pulmonary artery pressure, left atrial pressure, RV pressure, LV coronary pressure, blood temperature, blood oxygen saturation, one or more heart sounds, physical activity or exertion level, physiologic response to activity, posture, respiration, body weight, or body temperature.

The arrangement and functions of these leads and electrodes are described above by way of example and not by way of limitation. Depending on the need of the patient and the capability of the implantable device, other arrangements and uses of these leads and electrodes are possible.

As illustrated, the CRM system 100 can include a hemodynamic sensor-based AF event detection circuit 113. The hemodynamic sensor-based AF event detection circuit 113 can be configured to detect hemodynamic status of the patient. The hemodynamic sensor-based AF event detection circuit 113 can use the detected hemodynamic status, along with other physiologic signals sensed from the patient such as an output indicative of heart rate, to detect an AF onset event or an AF termination event. Examples of hemodynamic sensor-based AF event detection circuit 113 are described below, such as with reference to FIGS. 2-5.

The external system 120 can allow for programming of the IMD 110 and can receive information about one or more signals acquired by IMD 110, such as can be received via a communication link 103. The external system 120 can include a local external IMD programmer. The external system 120 can include a remote patient management system that can monitor patient status or adjust one or more therapies such as from a remote location.

The communication link 103 can include one or more of an inductive telemetry link, a radio-frequency telemetry link, or a telecommunication link, such as an internet connection. The communication link 103 can provide for data transmission between the IMD 110 and the external system 120. The transmitted data can include, for example, real-time physiological data acquired by the IMD 110, physiological data acquired by and stored in the IMD 110, therapy history data or data indicating IMD operational status stored in the IMD 110, one or more programming instructions to the IMD 110 such as to configure the IMD 110 to perform one or more actions that can include physiological data acquisition such as using programmably specifiable sensing electrodes and configuration, device self-diagnostic test, or delivery of one or more therapies.

The hemodynamic sensor-based AF event detection circuit 113 can be implemented at the external system 120 such as using data extracted from the IMD 110 or data stored in a memory within the external system 120. Portions of the hemodynamic sensor-based AF event detection circuit 113 may be distributed between the IMD 110 and the external system 120.

Portions of the IMD 110 or the external system 120 can be implemented using hardware, software, or any combination of hardware and software. Portions of the IMD 110 or the external system 120 may be implemented using an application-specific circuit that can be constructed or configured to perform one or more particular functions, or can be implemented using a general-purpose circuit that can be programmed or otherwise configured to perform one or more particular functions. Such a general-purpose circuit can include a microprocessor or a portion thereof, a microcontroller or a portion thereof, or a programmable logic circuit, or a portion thereof. For example, a "comparator" can include, among other things, an electronic circuit comparator that can be constructed to perform the specific function of a comparison between two signals or the comparator can be implemented as a portion of a general-purpose circuit that can be driven by a code instructing a portion of the general-purpose circuit to perform a comparison between the two signals. While described with reference to the IMD 110, the CRM system 100 could include a subcutaneous medical device (e.g., subcutaneous ICD, subcutaneous diagnostic device), wearable medical devices (e.g., patch based sensing device), or other external medical devices.

Figure 2:
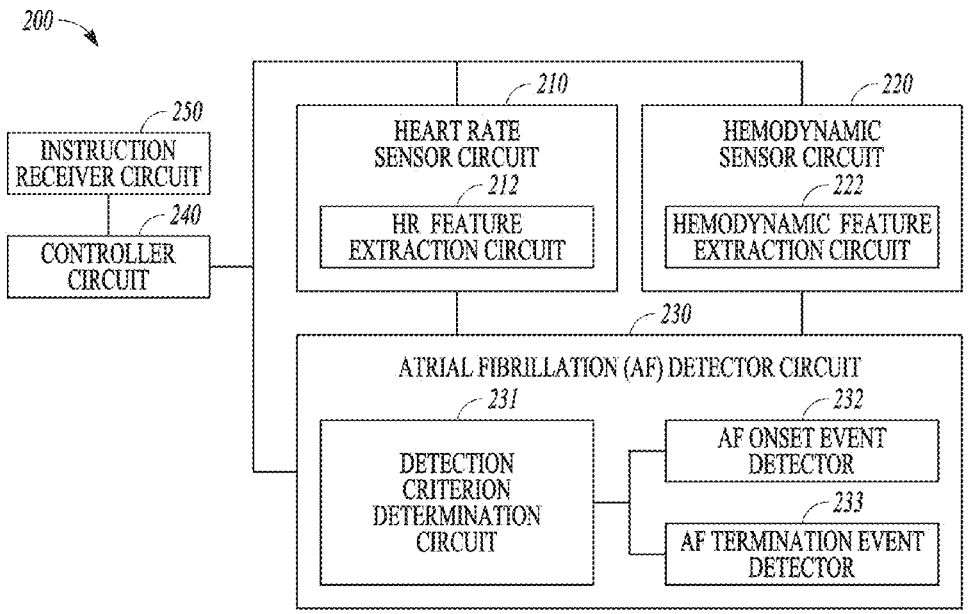
FIG. 2 illustrates an example of a hemodynamic sensor-based AF detector circuit.

FIG. 2 illustrates an example of a hemodynamic sensor-based AF detector circuit 200, which can be an embodiment of the hemodynamic sensor-based AF event detection circuit 113. The hemodynamic sensor-based AF detector circuit 200 can alternatively be implemented in an external system such as a patient monitor configured for providing diagnostic information to an end-user. The hemodynamic sensor-based physiologic event detector circuit 200 can include one or more of a heart rate sensor circuit 210, a hemodynamic sensor circuit 220, an atrial fibrillation (AF) detector circuit 230, a controller circuit 240, and an instruction receiver circuit 250.

The heart rate sensor circuit 210 can be configured to sense a heart rate output indicative of a heart rate of the patient. The heart rate sensor circuit 210 can include one or more implantable, wearable, or otherwise ambulatory cardiac activity sensor configured to sense cardiac electrical activity. In an example, the cardiac activity sensor can include electrodes on one or more of the leads 108A-C or the can 112. The electrodes are configured for sensing one or more electrograms (EGM) from inside the heart chamber, inside the heart tissue, on or near the surface of the heart. The electrodes can be non-invasively attached to the skin to sense a surface electrocardiogram (ECG). The electrodes can also placed subcutaneously (e.g., under the skin) to sense a subcutaneous ECG.

The heart rate sensor circuit 210 can include one or more amplifiers, analog to digital converters, filters, or other signal conditioning circuits that can process the sensed cardiac electrical activity, such as an ECG, a subcutaneous ECG, or an EGM. The heart rate sensor circuit 210 can detect from the processed cardiac electrical activity signals electrophysiological events such as events indicative of depolarization or repolarization of a specified portion of the heart, such as an atrium, a ventricle, a His-bundle, or a septum. Examples of the sensed atrial depolarization events can include P waves sensed from an ECG or a subcutaneous ECG signal, or atrial sensing events from an atrial EGM. Examples of the sensed ventricular depolarization events can include R waves sensed from an ECG or a subcutaneous ECG signal, or ventricular sensing events from a ventricular EGM.

Alternatively or additionally, the heart rate sensor circuit 210 can include one or more implantable, wearable, or otherwise ambulatory cardiac activity sensor configured to sense cardiac mechanical activity such as contractions of the heart. In an example, the cardiac activity sensor can include an accelerometer or a microphone configured to sense heart sound signal in a patient. In another example, the cardiac activity sensor can include an impedance sensor configured to sense variations of intracardiac impedance as a result of cyclic cardiac contractions. In addition to sensing directly the contractions of the heart, the cardiac activity sensor can also be configured to sense a physiologic activity caused by or correlative of cardiac contractions. For example, the heart rate sensor circuit 210 can include a blood pressure sensor or a blood flow sensor that can sense pulsatile arterial pressure or flow as a result of cyclic cardiac contractions and opening/closure of heart valves. The heart rate sensor circuit 210 can include one or more amplifiers and signal conditioning circuits, coupled to the cardiac mechanical activity sensors, which can process the sensed cardiac mechanical activity and detect mechano-physiologic events indicative of one or more of atrial contraction, ventricular contraction, end of filling, end of emptying, or other specified phase during a cardiac contraction cycle. Examples of the mechano-physiologic events can include: S1, S2, S3, or S4 heart sound from the sensed heart sound signal, peak or trough impedance from the cardiac impedance signal, or peak or trough blood pressure from the blood pressure signal, among others.

In some examples, the cardiac electrical or cardiac mechanical signals can be acquired from a patient and stored in a storage device such as an electronic medical record (EMR) system. The heart rate sensor circuit 210 can be coupled to the storage device and retrieve from the storage device one or more cardiac electrical or cardiac mechanical signals in response to a command signal. The command signal can be issued by an end-user such as via an input device coupled to the instruction receiver 250. The command signal can also be generated automatically by the system in response to occurrence of a specified event.

The heart rate sensor circuit 210 can include a heart rate (HR) feature extraction circuit 212 configured to generate one or more heart rate features such as by using the detected electrophysiological events or the detected mechano-physiologic events. In an example, the HR feature can include a cardiac cycle length (CL) or a HR derived from the cardiac cycle (e.g., HR=60/CL). The CL can be measured using the detected electrophysiological events such as an interval between two adjacent R waves (R-R interval) or P waves (P-P interval), an interval between adjacent impedance peaks or adjacent impedance troughs from the cardiac impedance signal, or an interval between two adjacent blood pressure peaks (i.e., systolic pressure) or adjacent blood pressure troughs (i.e., diastolic pressure) from the blood pressure signal.

The heart rate sensor circuit 210 can take a plurality of measurements of HR or CL at different time instances, and the heart rate feature extraction circuit 212 can generate the HR features as a statistical index derived from the plurality of measurements of HR or CL. In an example, the heart rate feature can include signal mean, median, or other central tendency measures of a plurality of the heart rate or CL measured over a specified period of time. In another example, the heart rate feature can include a variability of heart rate or variability of cardiac cycle length, or higher order statistics computed from the plurality of the heart rate CL measurements.

The hemodynamic sensor circuit 220 can be configured to sense a hemodynamic status output indicative of a hemodynamic status of the patient. The hemodynamic sensor circuit 220 can be coupled, through wired or wireless connection, to a hemodynamic sensor deployed on or inside the patient's body. The hemodynamic sensor can include an implantable, wearable, or otherwise ambulatory physiologic sensor that directly or indirectly measures dynamics of the blood flow in the heart or in the blood vessels. Examples of the hemodynamic sensor and physiologic variables to sense can include pressure sensors configured for sensing arterial pressure, pulmonary artery pressure, left atrial pressure, RV pressure, LV coronary pressure; impedance sensors configured for sensing thoracic impedance or cardiac impedance; temperature sensor configured for sensing blood temperature; accelerometers or microphones configured for sensing one or more heart sounds; optical sensors such as pulse oximeters configured for sensing blood oxygen saturation; chemical sensors configured for sensing central venous pH value. In an example, the sensing of hemodynamic status output is initiated in response to an automatically generated hemodynamic sensing command signal. The hemodynamic sensing command can be issued in response to the heart rate output meeting a specified rate criterion such as when the HR exceeds a specified threshold.

In some examples, the hemodynamic signals can be acquired from a patient and stored in a storage device such as an electronic medical record (EMR) system. The hemodynamic sensor circuit 220 can be coupled to the storage device and retrieve from the storage device one or more hemodynamic signals in response to a command signal. The command signal can be issued by a system user (e.g., a physician) such as via an input device coupled to the instruction receiver 250, or generated automatically by the system in response to a specified event.

The hemodynamic sensor circuit 220 can include a hemodynamic feature extraction circuit 222 configured to generate one or more hemodynamic features from a plurality of measurements of a physiologic variable such as measured from different time instants. Similar to the HR feature extraction circuit 212, the hemodynamic feature extraction circuit 222 can generate the hemodynamic features as a statistical index derived from the plurality of measurements of the physiologic variables, such as mean, median or other central tendency measures, or second order statistics including variability of the measurements, a histogram of the hemodynamic feature intensity, or higher order statistics of the measurements. Alternatively or additionally, the hemodynamic feature extraction circuit 222 can generate a hemodynamic feature using one or more signal trends of the physiologic parameter, such as intensity of the physiologic parameter over time, one or more signal morphological descriptors, or signal power spectral density at a specified frequency range. Examples of hemodynamic sensor circuit 220 are described below, such as with reference to FIG. 3.

The atrial fibrillation (AF) detector circuit 230 can be communicatively coupled to the heart rate sensor circuit 210 and the hemodynamic sensor circuit 220, and use at least the HR features provided by the heart rate sensor circuit 210 and the hemodynamic features provided by the hemodynamic sensor circuit 220 to detect an AF episode. The AF detector circuit 230 can include a detection criterion determination circuit 231, an AF onset event 232, and an AF termination event detector 233. The detection criterion determination circuit 231 can be configured to determine or receive detection criteria used for detecting onset and termination of an AF episode. The detection criterion determination circuit 231 can determine or receive a first detection criterion and a different second detection criterion, wherein the first detection criterion is more sensitive to the AF episode than the second detection criterion, and the second detection criterion is more specific to the AF episode than the first detection criterion. The first detection criterion can include a heart rate criterion, and the second detection criterion can include a hemodynamic status criterion. The AF onset event detector 232 can detect the AF onset event when the heart rate output meets the heart rate criterion, and the AF termination event detector 233 can detect the AF termination event when the hemodynamic status output meets the hemodynamic status criterion.

In an example, the detection criterion determination circuit 231 can determine or receive a first heart rate criterion, a different second heart rate criterion, a first hemodynamic status criterion, and a different second hemodynamic status criterion. The first heart rate criterion and the first hemodynamic status criterion can be used by the AF onset event detector 232 to detect an AF onset event. The second heart rate criterion and the second hemodynamic status criterion can be used by the AF termination event detector 233 to detect an AF termination event. The detection criterion determination circuit 231 can also receive instructions from an end-user to modify or confirm the automatically determined detection criteria.

The first heart rate criterion can be different from the second heart rate criterion, such that the first heart rate criterion is more sensitive to the presence of the AF episode than the second heart rate criterion, and the second heart rate criterion is more specific to the presence of the AF episode than the first heart rate criterion. Such a difference in heart rate criterion for AF onset and AF termination detection can reduce the chance of missing an AF onset event indicative of a beginning of a potential AF episode, thereby allowing a highly sensitive detection of the presence of AF episode. It can also reduce the chance of erroneously declaring sustaining of the detected AF episode, thereby allowing a highly specific detection of the AF episode with reduced false positive declaration of the presence of the AF episode.

The difference between the first and second heart rate criteria can be achieved by choosing different conditions for an extracted HR feature such as provided by the HR feature extraction circuit 212. In one example, the extracted HR feature includes a characteristic HR such as an average of a plurality of HR measurements or CL measurements over a specified period of time. The detection criterion determination circuit 231 can automatically determine the first heart rate criterion including a first heart rate threshold value ($HR_{TH1}$) and a second heart rate criterion including a second heart rate threshold value ($HR_{TH2}$) which is greater than $HR_{TH1}$. The extracted HR feature can also include a measure of spreadness or variability of a plurality of HR or CL measurements over a specified period of time. One example of the spreadness measure can include first-order statistics such as an average of beat-to-beat difference in HR or CL measurements, second-order statistics such as a variance or a standard deviation, or higher-order statistics of the HR or CL measurements. Another example of the spreadness measure can include geometric features extracted from a two dimensional scatter plot between two successive HR or CL measurements (e.g., CL(n) vs. CL(n−1)) or from a higher dimensional scatter plot among three or more HR or CL measurements (e.g., CL(n) vs. CL(n−1) vs. CL(n−2)). The detection criterion determination circuit 231 can automatically determine the first heart rate criterion including a first variability threshold value ($HRV_{TH1}$) and the second heart rate criterion including a second variability threshold value ($HRV_{TH2}$) which can be greater than $HRV_{TH1}$.

The detection criterion determination circuit 231 can determine the first and second heart rate threshold values ($HR_{TH1}$ and $HR_{TH2}$) or the first and second HRV threshold values ($HRV_{TH1}$ and $HRV_{TH2}$) based on empirical knowledge such as population-based statistics of the heart rate or statistics of the variability of heart rate from a group of patients experiencing AF episodes. Alternatively or additionally, the HR threshold values or HRV threshold values can be determined based on patient-specific statistics of the heart rate or statistics of the variability of heart rate calculated using the patient's historical AF episodes. Such statistics can be stored in a memory circuit and is retrievable or otherwise made available to the detection criterion determination circuit 231. In an example, if the population-based statistics or the patient-specific statistics indicate that the heart rate during AF is X bpm or the variability of heart rate during AF is Y bpm, the detection criterion determination circuit 231 can automatically determine the $HR_{TH1}$ to be lower than X (e.g., $HR_{TH1}$=X−a where a>0) and the $HR_{TH2}$ to be at or close to X, such that $HR_{TH1}$<$HR_{TH2}$. Similarly, the detection criterion determination circuit 231 can automatically determine the $HRV_{TH1}$ to be lower than Y (e.g., $HRV_{TH1}$=Y−b where b>0) and the $HRV_{TH2}$ to be at or close to Y, such that $HRV_{TH1}$<$HRV_{TH2}$. As an example, $HR_{TH1}$ is approximately in the range of 120-150 beats per minute (bpm), $HR_{TH2}$ is approximately in the range of 150-170 bpm, $HRV_{TH1}$ is approximately in the range of 20-50 bpm, and $HRV_{TH2}$ is approximately in the range of 50-90 bpm.

The difference between the first and second heart rate criteria can also be achieved by choosing different HR features such as provided by the HR feature extraction circuit 212. A HR feature that is more sensitive to presence of an AF episode can be used for AF onset detection, and a HR feature that is more specific to the presence of the AF episode can be used for AF termination detection. For example, a short-term average of HR measurements can be a HR feature sensitive to the presence of AF episode, and a combination of a long-term average of HR measurements and the variability of the HR measurements can be HR features specific to the presence of AF episode. Therefore, the detection criterion determination circuit 231 can determine the first heart rate criterion to be a short-term average of HR exceeding $HR_{TH1}$, while determine the second heart rate criterion to be both a long-term average of HR falling below $HR_{TH2}$ and the variability of the HR falling below $HRV_{TH2}$.

The detection criterion determination circuit 231 can automatically determine the first and second hemodynamic status criteria according to the hemodynamic features extracted from the hemodynamic sensors, such as those provided by the hemodynamic feature extraction circuit 222. In an example, the first and second hemodynamic status criteria respectively include a first and a second hemodynamic status threshold value. The first and second hemodynamic status threshold value can be determined based on empirical knowledge such as population-based statistics of the extracted hemodynamic features from a group of patients experiencing AF episodes, or alternatively or additionally based on patient-specific statistics of the extracted hemodynamic features from the patient's historical AF episodes. In some examples, the first and second hemodynamic status criteria can differ from each other. The difference between the first and second hemodynamic status criteria can be achieved by choosing different conditions for an extracted hemodynamic feature. The difference between the first and second hemodynamic status criteria can also be achieved by choosing different hemodynamic features such as provided by the hemodynamic feature extraction circuit 222. In an example, the extracted hemodynamic features can include a heart sound feature indicative of cardiac hemodynamic status during AF. The detection criterion determination circuit 231 can determine the first and second threshold values relating to a heart sound feature, as described below such as with reference to FIG. 3.

The AF onset event detector 232 and the AF termination detector 233 can both be coupled to the detection criterion determination circuit 231. The AF onset event detector 232 detect an AF onset event when the heart rate feature received from the HR feature extraction circuit 212 meets the first heart rate criterion and the hemodynamic status output received from the hemodynamic feature extraction circuit 222 meets the first hemodynamic status criterion. The AF termination event detector 233 detect an AF termination event when a heart rate feature received during a detected AF episode meets the second heart rate criterion and a hemodynamic status feature received during the detected AF episode meets the second hemodynamic status criterion. Examples of AF onset detector 232 and AF termination detector 233 are described below, such as with reference to FIGS. 4A and 4B.

The controller circuit 240 can receive external programming input from the instruction receiver circuit 250 to control the operations of the heart rate sensor circuit 210, the hemodynamic sensor circuit 220, the AF detector circuit 230, and the data flow and instructions between these components. Examples of the instructions received by instruction receiver 250 can include one or more of sensing of cardiac electrical or mechanical activity signals, extracting HR features, sensing of hemodynamic status signals, extracting hemodynamic features, confirming or modifying the automatically determined detection criteria, or detecting the AF onset or AF termination. The instruction receiver circuit 250 can include a user interface configured to present programming options to the user and receive system user's programming input. In an example, at least a portion of the instruction receiver circuit 250, such as the user interface, can be implemented in the external system 120.

The hemodynamic sensor-based AF detector circuit 200 can optionally include a therapy delivery system configured to provide and deliver therapy to the patient in response to a detection of the AF onset event such as provided by the AF onset event detector 232, or to withhold the therapy to the patient in response to a detection of the AF termination event such as provided by the AF termination event detector 233. The therapy can include one or more of a cardiac stimulation therapy, a cardiac ablation therapy, a neurostimulation therapy, or pharmacological therapy, among other therapy modalities. In an example, the cardiac stimulation therapy can be in a form of electrostimulation to a target tissue inside or on the heart, including an endocardium or an epicedium of an atrium or a ventricle. The electrostimulation can be delivered via one or more of the leads 108A-C or the can 112. Examples of electrostimulation therapy can include ventricular rate regularization pacing, atrial anti-tachycardia pacing, atrial cardioversion therapy, or atrial defibrillation therapy.

Figure 3:
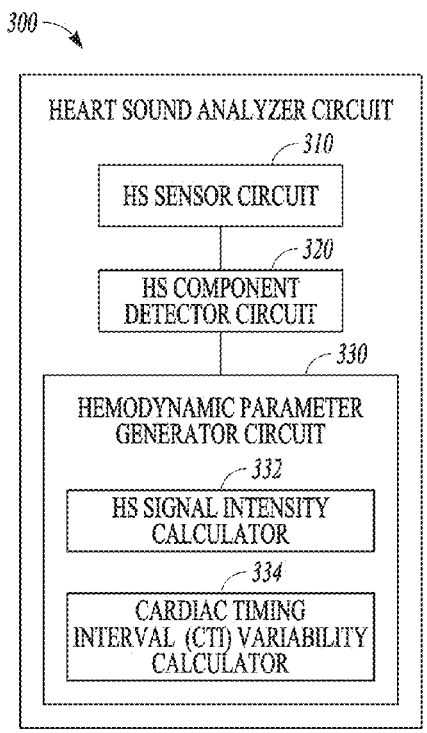
FIG. 3 illustrates an example of a heart sound analyzer circuit.

FIG. 3 illustrates an example of a heart sound (HS) analyzer circuit 300, which can be an embodiment of the hemodynamic sensor circuit 220. The HS analyzer circuit 300 can be configured to generate one or more HS features indicative or correlative of hemodynamic status of the patient. The heart sound analyzer circuit 300 can include a heart sound sensor circuit 310, a HS component detector circuit 320, and a hemodynamic parameter generator circuit 330.

The HS sensor circuit 310 can be coupled to a heart sound sensor that can detect the heart sound or other forms of signals generated as a result of mechanical activities of the heart such as contraction and relaxation. Examples of the HS sensors can include an ambulatory accelerometer or an ambulatory microphone. The heart sound sensor can be external to the patient or implanted inside the body. In an example, the heart sound sensor can be within an ambulatory medical device such as the IMD 110.

The HS component detector circuit 320 can process the sensed HS signal, including amplification, digitization, filtering, or other signal conditioning operations. In an example, the HS component detector circuit 320 can include one or more a low-pass, high-pass, or band-pass filters that can filter the sensed HS signal to a specified frequency range. For example, the HS component detector circuit 320 can include a bandpass filter adapted to filter the HS signal to a frequency range of approximately between 5 and 90 Hz. In another example, the HS component detector circuit 320 includes a bandpass filter adapted to filter the HS signal to a frequency range of approximately between 9 and 90 Hz. In an example, the HS component detector circuit 320 can include a double or higher-order differentiator configured to calculate a double or higher-order differentiation of the sensed heart sound signal.

The HS component detector circuit 320 can further detect, using the processed HS signal, one or more HS components including S1, S2, S3 or S4 heart sounds. In an example, the HS component detector circuit 320 can generate respective time windows for detecting one or more HS components. The time windows can be determined with reference to a physiologic event such as Q wave, R wave, or QRS complexes detected from a surface ECG or a subcutaneous ECG, or an atrial or a ventricular sensing event in an intracardiac EGM. For example, an S1 detection window can begin at 50 milliseconds (msec) following a detected R wave and have a duration of 300 msec. An S2 detection window can begin at specified offset following a detected R wave or S1 heart sound. An S3 detection window can be determined using at least one cardiac signal feature such as the R-wave timing or the timing of S2 heart sound. The S3 detection window can have a specified duration and can begin at a specified offset following the detected S2. In an example, the offset can be 125 msec, and the S3 window duration can be 125 msec. The offset or the S3 window duration can be a function of a physiologic variable such as a heart rate. For example, the offset can be inversely proportional to the heart rate, such that the S3 detection window can start at a smaller offset following the S2 at a higher heart rate.

The HS component detector circuit 320 can detect an HS component from at least a portion of the HS signal within the respective HS detection window. In an example, HS signal energy within a S2 detection window can be computed and compared to a S2 energy threshold, and an S2 component is detected in response to the HS signal energy exceeds the S2 energy threshold. In an example, the HS component detector circuit 320 can detect an HS component adaptively by tracking the temporal locations of the previously detected HS features. For example, an S3 heart sound can be detected by adaptively tracking the timing of historically detected S3 heart sounds. A dynamic programming algorithm can be used to detect and track the S3 heart sound within the S3 detection window, such as that disclosed in the commonly assigned Patangay et al. U.S. Pat. No. 7,853,327 entitled "HEART SOUND TRACKING SYSTEM AND METHOD," which is hereby incorporated by reference in its entirety.

The hemodynamic parameter generator circuit 330 can generate one or more hemodynamic parameters using one or more of the HS features. The hemodynamic parameter generator circuit 330 can include a HS signal intensity calculator 332 configured to calculate an HS intensity indicative of signal strength of a HS component, such as intensity of an S1 heart sound (||S1||) or intensity of S2 heart sound (||S2||). Examples of the intensity of a HS component can include amplitude of a detected HS component in a time-domain HS signal, a transformed HS signal such as integrated HS energy signal, or in a frequency-domain HS signal such as the peak value of the power spectral density. In some examples, the hemodynamic parameter generator circuit 330 can be configured to measure the HS intensity as the peak value of a generic measurement within the respective HS detection window, such as peak envelop signal or root-mean-squared value of the portion of the HS signal within the HS detection window.

Alternatively or additionally, the hemodynamic parameter generator circuit 330 can include a cardiac timing interval variability calculator 334 configured to determine a variability of cardiac timing interval (CTIvar) using the sensed cardiac electrical activity and the detected HS component. The cardiac timing interval (CTI) can represent the timing interval between two cardiac events such as a cardiac electrical event detected from the cardiac electrical signal and a mechanical event such as detected from a cardiac mechanical signal or a hemodynamic signal such as heart sound signal.

The CTI can include a pre-ejection period (PEP), a systolic timing interval (STI), a left ventricular ejection time (LVET), or a diastolic timing interval (DTI), among others. The PEP represents the total duration of the electrical and mechanical events prior to ejection. The PEP can include the electrical-mechanical delay which occurs between the onset of the ventricular depolarization and the beginning of ventricular contraction, and the isovolumetric contraction time during which the left ventricle can contract prior to the opening of the aortic valve. The PEP can be measured using one or more physiologic signals. In an example, the PEP can be measured as the time duration from the onset of the QRS to the S1 heart sound, that is, PEP≈Q–S1 interval. The onset of the QRS can be determined from the ECG as the Q wave or the atrial activation event from the EGM such as the atrial EGM measured using one or more electrodes on the implantable lead 108A and the can 112. In another example, the PEP can be measured as the duration from the Q wave or the atrial activation event to the rise of the arterial pressure such as that measured from a carotid pulse wave. In an example, when no spontaneous QRS wave is present and the heart is electrically paced such as by using an IMD 110, the PEP can be measured from the ventricular pacing (Vp) signal to the beginning of ventricular ejection such as represented by the onset of S1 heart sound, that is, PEP≈Vp–S1 interval.

The STI represents the duration of total electro-mechanical systole. The STI spans from the electrical excitation of the heart to the closure of the aortic valve, and it contains two major components, namely the PEP and the LVET which represents the time interval from the opening to the closing of the aortic valve (mechanical systole). In an example, LVET can be measured as the period from S1 to S2 heart sounds. The STI can be measured using one or more physiologic signals sensed from physiologic sensors. Examples of the physiologic signals used for calculating STI or LVET include a heart sound signal, an intracardiac impedance signal, or a pressure signal. In an example, the STI can be measured as the interval from the onset of the QRS complex on the ECG or the atrial activation event in an intracardiac EGM to the S2 heart sound, that is, STI≈Q–S2 interval. In the case when the ventricle is paced (Vp), the STI can be measured from the ventricular pacing (Vp) signal to the end of ventricular ejection such as represented by the onset of S2 heart sound, that is, STI≈Vp–S2 interval.

The DTI represents the duration of total electro-mechanical diastole. The DTI spans from the closure of the aortic valve to the onset of the atrial depolarization in the next cardiac cycle. In an example, the DTI can be measured as the interval from the S2 heart sound to the onset of the QRS complex on the ECG or the atrial activation event in an intracardiac EGM of the next cardiac cycle, that is, DTI≈S2–Q interval. Therefore, a STI and the following DTI span the cardiac cycle, that is, CL=STI+DTI.

The CTI can also include composite measures using two or more of the STI, the DTI, the PEP, the cardiac cycle (CL), or the LVET. Examples of the composite measures can include PEP/LVET ratio, STI/DTI ratio, STI/CL ratio, or DTI/CL ratio, among others. The irregular ventricular activity during AF can also lead increased variability of one or more of CTI measures. For example, the inappropriately irregular ventricular electrical excitation and mechanical contraction during AF can result in fluctuation in diastolic filing time, i.e., the DTI. The increased variability of DTI can further lead to widely varying stroke volume, thereby deteriorating patient's hemodynamic stability. As such, the variability of cardiac timing interval (CTIvar), such as the variability of STI (STIvar), the variability of the DTI (DTIvar), or the variability of the PEP (PEPvar), can be indicative of the cardiac hemodynamics; and used in detecting AF onset by the AF onset event detector 232 or detecting AF termination by the AF termination event detector 233.

In accordance with the hemodynamic parameters generated in 330, the detection criterion determination circuit 231 can automatically determine first ($HS_{TH1}$) and second ($HS_{TH2}$) threshold values of the intensity of the heart sound component, or first ($DTIvar_{TH1}$) and second ($DTIvar_{TH2}$) threshold values of DTIvar. For example, the AF onset event detector 232 can detect the AF onset event when the heart rate output meets the first heart rate criterion, and either the computed HS component intensity falls below the $HS_{TH1}$ or the computed DTIvar exceeds the $DTIvar_{TH1}$. Likewise, the AF termination event detector 233 can detect the AF termination event when the heart rate output meets the second heart rate criterion, and either the computed HS component intensity exceeds the $HS_{TH2}$, or the DTIvar falls below the $DTIvar_{TH2}$. As an alternative to DTIvar and the associated thresholds, other variability of the cardiac timing intervals including STIvar or PEPvar and the respective thresholds can also be used by the AF onset event detector 232 or the AF termination event detector 233 to respectively detect onset or termination of the AF episode.

Figure 4A:
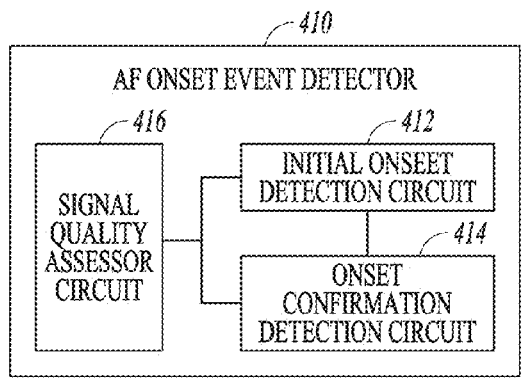
FIGS. 4A-B illustrate respectively examples of an AF onset event detector and an AF termination event detector
Figure 4B:
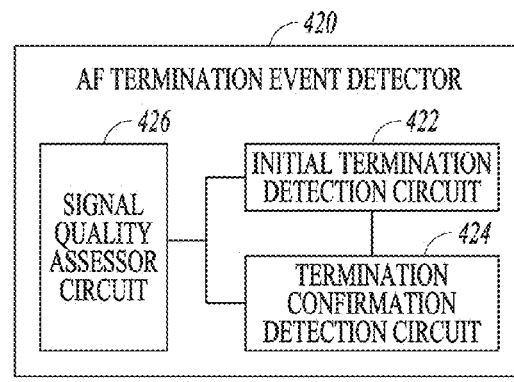

FIG. 4A illustrates an example of an AF onset event detector 410, and FIG. 4B illustrates an example of an AF termination event detector 420. The AF onset event detector 410 can be an embodiment of the AF onset event detector 232, and the AF termination event detector 420 can be an embodiment of the AF termination event detector 233.

The AF onset event detector 410 can include an initial onset detection circuit 412, an onset confirmation detection circuit 414, and a signal quality assessor circuit 416. The AF onset event detector 410 can detect the AF onset event through a two-stage cascade detection process including an initial AF onset event detection by the initial onset detection circuit 412 and a confirmation process by the onset confirmation detection circuit 414. In an example, the initial onset detection circuit 412 can determine whether the heart rate feature meets the first heart rate criterion such as provided by the detection criterion determination circuit 231, and the onset confirmation detection circuit 414, coupled to the initial onset detection circuit 412, can confirm or refute the initial detection of the AF onset event by determining whether the hemodynamic feature meets the first hemodynamic status criterion such as provided by the detection criterion determination circuit 231.

The signal quality assessor circuit 416 can analyze the HR features (such as those provided by the HR feature extraction circuit 212) and the hemodynamic features (such as those provided by the hemodynamic feature extraction circuit 222), and generate respective quality indices for the HR features and the hemodynamic features. The signal quality assessor circuit 416 can also receive from the heart rate sensor circuit 210 information about quality of the cardiac activity signals used for generating the HR features, or from the hemodynamic sensor circuit 220 information about quality of the hemodynamic status signals used for generating the hemodynamic features. The signal quality index can be computed as signal strength, noise or interference level, or signal to noise ratio (SNR) of a cardiac signal. The signal quality index can also be computed based on a comparison of two signals such as obtained from two sensors. In an example, the quality index of a HR feature can be determined as a level of consistency between the HR feature computed using a cardiac electrical signal (e.g., an intracardiac EGM) and the HR feature computed using a cardiac mechanical signal (e.g., an impedance or heart sound signal).

The initial onset detection circuit 412 and the onset confirmation detection circuit 414, coupled to the signal quality assessor circuit 416, can each use the information of the signal quality to adjust the detection criteria provided by the detection criterion determination circuit 231. In one example, the initial onset detection circuit 412 can choose a HR feature in initial detection only if the quality index (e.g., an SNR) of the cardiac electrical or mechanical activity signal exceeds a specified threshold. Likewise, the onset confirmation detection circuit 414 can choose a hemodynamic feature in confirmation detection only if the quality index (e.g., SNR) of the hemodynamic sensor signal exceeds a specified threshold. In another example, if the signal quality index of the HR feature fails to meet a specified threshold, the initial AF onset detection can be bypassed (or a default positive initial detection is determined), and the confirmation detection is performed directly by the onset confirmation detection circuit 414.

Similar to the AF onset event detector 410, the AF termination event detector 420 can include an initial termination detection circuit 422, a termination confirmation detection circuit 424, and a signal quality assessor circuit 426. The AF termination event detector 420 can detect the AF termination event through a two-stage cascade detection process, including an initial termination detection by the initial detection circuit 422 and a confirmation detection by the termination confirmation detection circuit 424. The second heart rate criterion used in initial termination detection circuit 422 can be more specific, but less sensitive, to the presence of an AF episode than the first heart rate criterion used in initial onset detection circuit 412.

Similar to FIG. 4A, the signal quality assessor circuit 426, coupled to the initial termination detection circuit 422 and the termination confirmation detection circuit 424, can provide quality indices of the HR features or hemodynamic features, the initial termination detection circuit 422 can choose a HR feature in initial detection only if the quality index of the cardiac electrical or mechanical activity signal exceeds a specified threshold. Likewise, the termination confirmation detection circuit 424 can choose a hemodynamic feature in confirmation detection only if the quality index of the hemodynamic sensor signal exceeds a specified threshold. If the signal quality index of the HR feature fails to meet a specified threshold, the initial AF termination detection can be bypassed and the confirmation detection circuit 424 directly performs confirmation detection.

Figure 5:
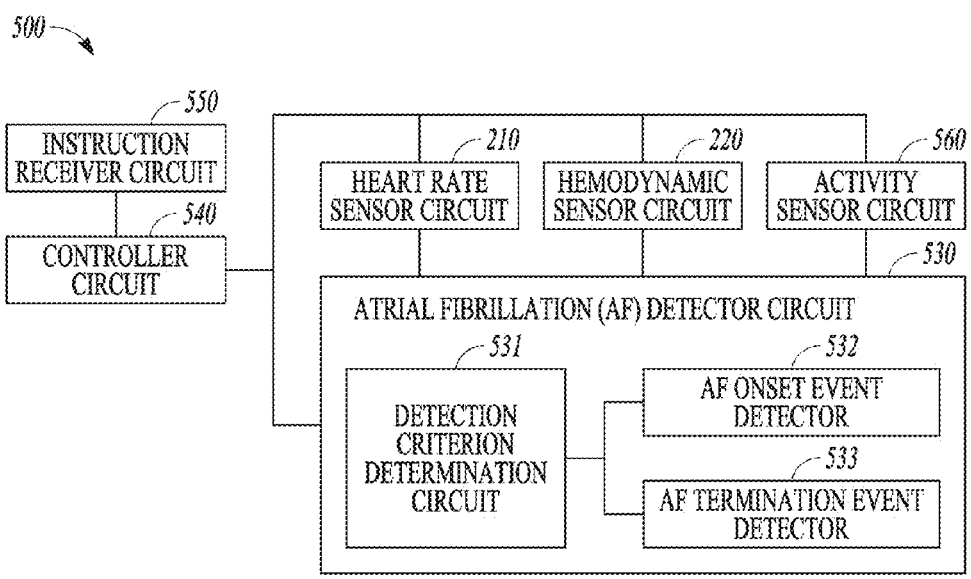
FIG. 5 illustrates an example of a heart sound-based AF detector circuit.

FIG. 5 illustrates an example of a heart sound-based AF detector circuit 500, which can be an embodiment of the hemodynamic sensor-based AF event detection circuit 113. The heart sound-based AF detector circuit 500 can also be implemented in an external system such as a patient monitor configured for providing the patient's diagnostic information to an end-user. The heart sound-based physiologic event detector circuit 500 can include one or more of a heart rate sensor circuit 210, a hemodynamic sensor circuit 220, an activity sensor circuit 560, an AF detector circuit 530, a controller circuit 540, and an instruction receiver circuit 550.

As illustrated in FIG. 5, the heart sound-based AF detector circuit 500 has a configuration similar to the sound-based AF detector circuit 200. The discussion of the sound-based AF detector circuit 200 such as with reference to FIG. 2, including the one or more of a heart rate sensor circuit 210 and the hemodynamic sensor circuit 220 and the embodiments of various components therein such as with reference to FIGS. 3 and 4A-4B, are hereby incorporated in their entirely.

The activity sensor circuit 560 can be configured to sense physical activity or exertion level output of the patient, including vigorousness or duration of the activity. In an example, the activity sensor circuit 560 can be communicatively coupled to an ambulatory accelerometer and sense an acceleration signal from the patient. The activity sensor circuit 560 can process the sensed acceleration signal through a first signal processing circuit to generate the activity or exertion level output of the patient. The accelerometer can also be coupled to the hemodynamic sensor circuit 220, which is configured to process the sensed acceleration signal through a second signal processing circuit different from the first signal processing circuit, and to generate a heart sound signal indicative of hemodynamic status of the patient. In various examples, the activity sensor circuit 560 can include respiration sensor configured to sense physiologic response to activity including respiration rate signal, tidal volume signal, minute ventilation signal, or apnea-hypopnea index, among other signals. Examples of the respiration sensor can include an impedance sensor configured to sense a thoracic impedance signal indicative of ventilation level of the patient.

The detection criterion determination circuit 531 can automatically determine a first heart rate criterion, a different second heart rate criterion, a first hemodynamic status criterion, a different second hemodynamic status criterion, a first activity or exertion level criterion, and a different second activity or exertion criterion. In an example, one or more of the heart rate criteria, hemodynamic status criteria, or the activity or exertion criteria can include respective threshold values that can be determined based on population-based statistics or patient-specific statistics. The first heart rate criterion can be more sensitive to the presence of the AF episode than the second heart rate criterion, and the second heart rate criterion can be more specific to the presence of the AF episode than the first heart rate criterion.

The AF onset event detector 532 can be configured to detect an AF onset event when the heart rate output meets the first heart rate criterion, the hemodynamic status output meets the first hemodynamic status criterion, and the sensed activity or exertion level output meets the first activity or exertion criterion. In an example, the AF onset event detector 532 detects an AF onset event if an increase of the heart rate or an increase of variability of HR exceeds a first HR threshold, an acceleration or minute ventilation signals indicates a non-significant change in the activity or exertion level, and the HS intensity falls below a first HS threshold. Likewise, the AF termination event detector 533 can be configured to detect the AF termination event when the heart rate output meets the second heart rate criterion, the hemodynamic status output meets the second hemodynamic status criterion, and the sensed activity or exertion level output meets the second activity or exertion criterion.

Figure 6:
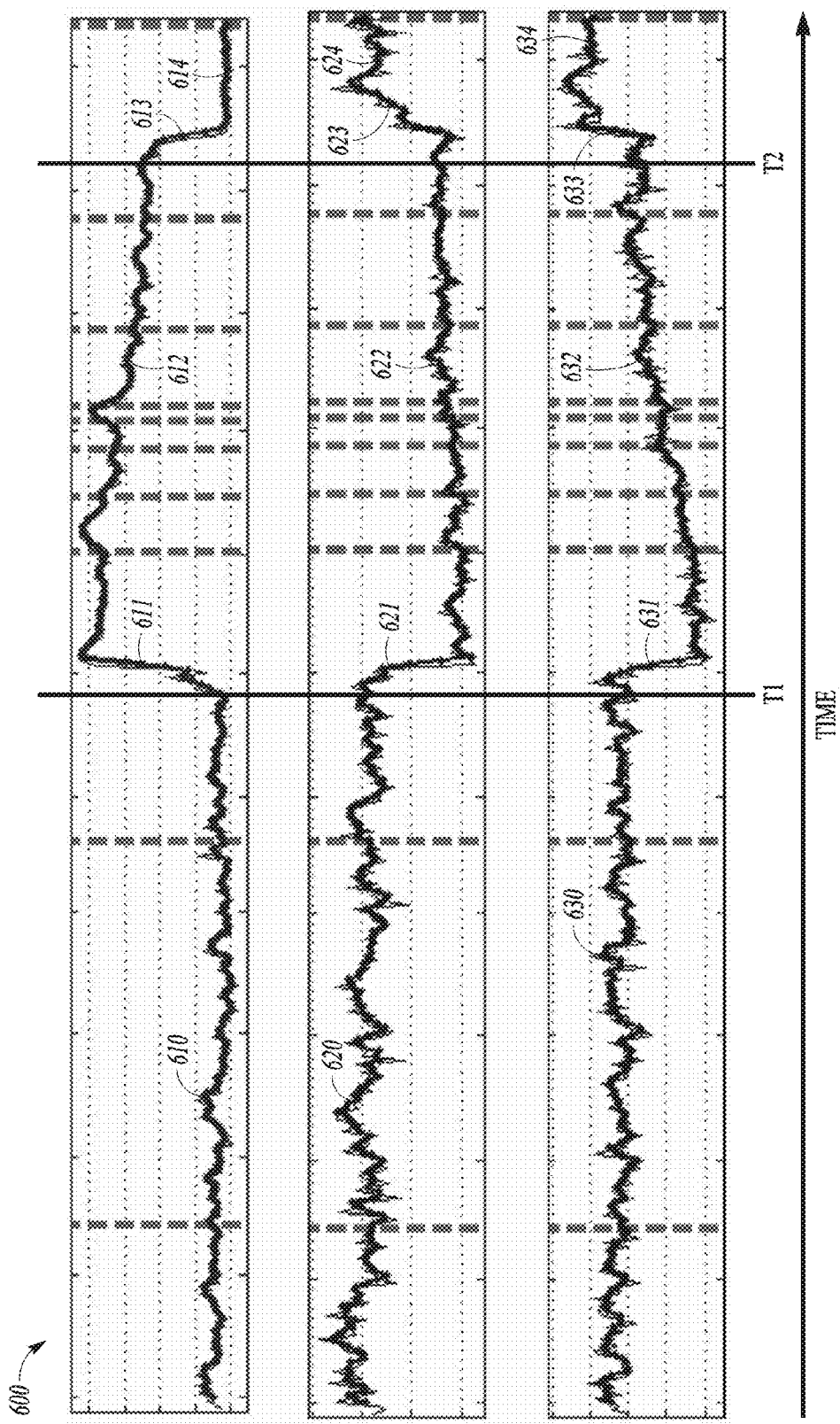
FIG. 6 illustrates an example of changes in heart rate and hemodynamic parameters during the onset and termination of an AF episode in a patient.

FIG. 6 illustrates an example 600 of changes in heart rate (HR) and hemodynamic parameters during the onset and termination of an AF episode in a patient. The daily average HR trend signal 610, which can be generate by the heart rate sensor circuit 210, represents temporal variation of the daily average HR over approximately 12 months. Drawn on the same time scale are a daily average S1 heart sound intensity (||S1||) trend signal 620 and a daily average S2 heart sound intensity (||S2||) trend signal 630. Signals 620 and 630 can be generated by the hemodynamic sensor circuit 220. The intensity signals ||S1|| and ||S2|| are each computed as the signal power of S1 or S2 over respective time window.

As illustrated in FIG. 6, in response to an AF onset event occurring at time instant T1, the heart rate increases at 611, the ||S1|| decreases at 621 and the ||S2|| decreases at 631. During the sustained AF episode (between T1 and T2), the HR signal 612 remains at an elevated level and gradually decreases. Both the ||S1|| and ||S2|| signals remain lower than their respective pre-AF level, but gradually recover during the AF episode. At time instant T2, an AF termination event occurs. In response to the AF termination event, the heart rate decreases at 613, the ||S1|| increases at 623, and ||S2|| increases at 633. Following the transitional phases of AF termination, the HR signal 614, the ||S1|| signal 624, and the ||S2|| signal 634 reach or exceed their respective pre-AF level.

Figure 7:
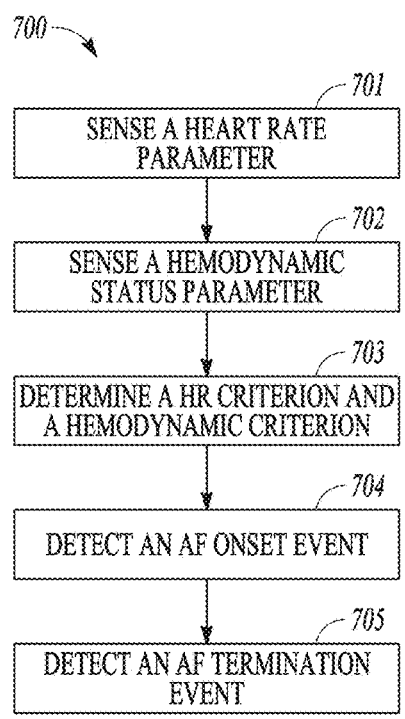
FIG. 7 illustrates an example of a method for detecting an AF onset event and an AF termination event in a patient.

FIG. 7 illustrates an example of a method 700 for detecting an AF onset event and an AF termination event in a patient. The method 700 can be implemented and operate in an ambulatory medical device or in a remote patient management system. In an example, the method 700 can be performed by the hemodynamic sensor-based AF event detection circuit 113 implemented in the IMD 110, or the external device 120 which can be in communication with the IMD 110.

At 701, a heart rate parameter can be sensed such as by using the heart rate sensor circuit 210. The heart rate parameter can include a heart rate, a cardiac cycle length (CL), or a statistical index derived from a plurality of measurements of HR or CL. Examples of the statistical index can include signal mean, median, or other central tendency measures of a plurality of the heart rate or CL measured over a specified period of time, or a variability of HR or variability of CL, or higher order statistics computed from the plurality of the heart rate CL measurements. The heart rate parameter can be sensed from a cardiac electrical signal such as a surface ECG, a subcutaneous ECG, or an intracardiac EGM. In an example, the HR or CL can be measured as an interval between adjacent R waves in an ECG (R-R interval), or an interval between adjacent ventricular sensed events in an intracardiac EGM (V-V interval). The heart rate parameter can also be sensed from a cardiac mechanical signal such as a heart sound signal, a cardiac impedance signal, or blood pressure signal. The HR or CL can be measured as an interval between adjacent mechanophysiologic events detected from a cardiac mechanical signal, such as an interval between two adjacent S1 heart sounds or between two adjacent S2 heart sounds, an interval between adjacent peaks or adjacent troughs of a cardiac impedance signal, or an interval between adjacent peaks or adjacent troughs of a blood pressure signal, among others.

At 702, a hemodynamic status parameter can be sensed such as by using the hemodynamic sensor circuit 220. Examples of the hemodynamic status parameter can include arterial pressure, pulmonary artery pressure, left atrial pressure, RV pressure, LV coronary pressure, thoracic impedance or cardiac impedance, blood temperature, one or more heart sound components including S1, S2, S3 or S4 heart sounds, blood oxygen saturation, or central venous pH value, among others. The hemodynamic status parameter can also include statistical indices derived from the plurality of measurements of the physiologic variables, such as mean, median or other central tendency measures, or second order statistics including variability of the measurements, a histogram of the hemodynamic feature intensity, or higher order statistics of the measurements. The hemodynamic status parameter can also include one or more signal trends of the physiologic parameter (such as intensity of the physiologic parameter over time), one or more signal morphological descriptors, or signal power spectral density at a specified frequency range.

At 703, AF detection criteria can be automatically determined, received as an input from an end-user, or stored and retrieved from a storage device. The AF detection criterion can include a first detection criterion and a different second detection criterion, wherein the first detection criterion is more sensitive to the AF episode than the second detection criterion, and the second detection criterion is more specific to the AF episode than the first detection criterion. In an example, the first detection criterion can include a heart rate criterion, and the second detection criterion can include a hemodynamic status criterion.

In another example, the AF detection criteria can include at least a first heart rate criterion, a different second heart rate criterion, a first hemodynamic status criterion, and a different second hemodynamic status criterion. The first heart rate criterion and the first hemodynamic status criterion can be used for detecting an AF onset event, and the second heart rate criterion and the second hemodynamic status criterion can be used for detecting an AF termination event. Automatic determination of AF detection criteria can be based on empirical knowledge such as population-based statistics of the heart rate or statistics of the variability of heart rate from a group of patients experiencing AF episodes, or alternatively or additionally based on patient-specific statistics of the heart rate or statistics of the variability of heart rate from a the patient's historical AF episodes. In some examples, the AF detection criteria can be presented to a system user such as via a user interface that allows the user to interactively review, modify, or confirm the automatically determined AF detection criteria.

The first heart rate criterion can be different from the second heart rate criterion, such that the first heart rate criterion is more sensitive to the presence of the AF episode than the second heart rate criterion, and the second heart rate criterion is more specific to the presence of the AF episode than the first heart rate criterion. Such a difference in heart rate criterion for AF onset and AF termination detection can reduce the chance of missing an AF onset event indicative of a beginning of a potential AF episode, thereby allowing a highly sensitive detection of AF episode. It can also reduce the chance of erroneously declaring sustaining of the detected AF episode, thereby allowing a highly specific detection of the AF episode with reduced false positive declaration of the presence of the AF episode.

The difference between the first and second heart rate criteria can be achieved by choosing different conditions for an extracted HR feature, such as different threshold values for HR. Alternatively or additionally, the difference between the first and second heart rate criteria can be achieved by choosing different HR features. A HR feature that is more sensitive to AF onset event can be used for AF onset detection, and a HR feature that is more specific to AF termination can be used for AF termination detection. In an example, the first heart rate criterion is a short-term average of HR exceeding the first HR threshold value $HR_{TH1}$, while the second heart rate criterion includes both a long-term average of HR falling below a second HR threshold value $HR_{TH2}$ and the variability of the HR falling below a second heart rate variability threshold value $HRV_{TH2}$.

At 704, an AF onset event can be detected. In an example, the AF onset event can be detected when the heart rate output meets the heart rate criterion. In another example, the AF onset event can be detected using the sensed heart rate parameter and the sensed hemodynamic status parameter. The AF onset event detection can include a two-stage cascade detection process comprising an initial detection and a confirmation detection. In an example, the initial detection includes a determination of whether the heart rate feature meets the first heart rate criterion, and the confirmation detection includes a confirmation or refutation of the initial detection of the AF onset event, based on a determination of whether the hemodynamic feature meets the first hemodynamic status criterion.

At 705, an AF termination event is detected. In an example, the AF termination can be detected when the hemodynamic status output meets the hemodynamic status criterion. In another example, the AF termination event can be detected using the sensed heart rate parameter and the sensed hemodynamic status parameter. Similar to the AF onset event detection at 704, the AF termination event detection can include a two-stage cascade detection process comprising an initial detection and a confirmation detection. The detection of AF termination can be initiated by an indication of an AF onset event being detected such as the heart rate feature meeting the second heart rate criterion, and the confirmation detection includes a confirmation or refutation of the initial detection of the AF termination event such as based on a determination of whether the hemodynamic feature meets the second hemodynamic status criterion.

The method 700 can optionally include delivering a specified therapy to the patient such as by using a therapy generation and delivery system in response to a detection of the AF onset event, or to withhold the therapy in response to a detection of the AF termination event. The therapy can include one or more of a cardiac stimulation therapy, a cardiac ablation therapy, a neurostimulation therapy, or pharmacological therapy. In an example, the cardiac stimulation therapy can be in a form of electrostimulation to a target inside or on the heart, including an endocardium or an epicedium of an atrium or a ventricle. Examples of electrostimulation therapy can include ventricular rate regularization pacing, atrial anti-tachycardia pacing, atrial cardioversion therapy, or atrial defibrillation therapy.

Figure 8:
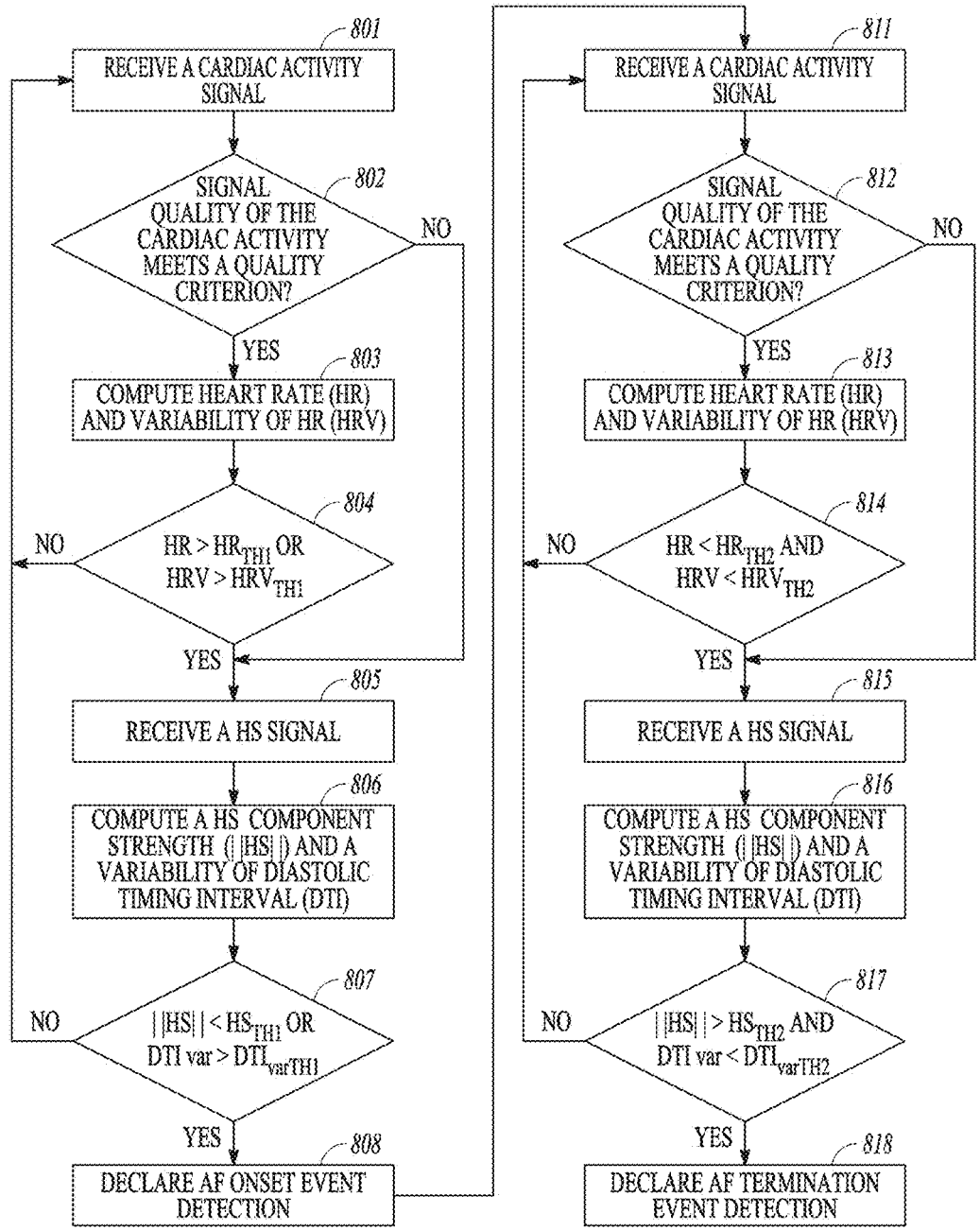
FIG. 8 illustrates an example of a method for detecting AF onset and AF termination using heart sounds and heart rate parameters.

FIG. 8 illustrates an example of a method 800 for detecting AF onset and AF termination using heart sounds and heart rate parameters. The method 800 can be an embodiment of the method 700 for detecting an AF onset event and an AF termination event. In an example, the method 800 can be performed by the hemodynamic sensor-based AF event detection circuit 113.

The method 800 can detect the AF onset event using a two-stage process, with a first stage of initial AF onset detection (801 through 804) using one or more heart rate features, and a second stage of AF onset event confirmation (805 through 807) using one or more heart sound features indicative of patient hemodynamic status. At 801, at least one cardiac activity signal can be received from a patient. The cardiac activity signal can include a cardiac electrical signal such as an intracardiac electrogram, surface electrocardiogram (ECG), or subcutaneous electrogram, or a cardiac mechanical signal such as a heart sound signal, a cardiac impedance signal, or blood pressure signal. At 802, the received cardiac activity signal is analyzed and a signal quality index can be computed. The signal quality index can be computed as signal strength, noise or interference level, or signal to noise ratio (SNR) of a cardiac activity signal. In an example where more than one cardiac activity signals are sensed at 801, signal quality of each of the sensed cardiac activity signal can be computed and compare to each other at 802, and the cardiac activity signal having the highest signal quality (e.g., highest SNR) can be selected for use at 803.

If the signal quality of the cardiac activity signal fails to meet a specified criterion (e.g., the SNR being lower than a specified threshold value), the cardiac activity signal is deemed noisy and the first stage of initial AF onset event detection can be bypassed; and the second stage of AF onset event confirmation can by initiated by receiving a heart sound signal at 806. However, if the signal quality of the cardiac activity signal does meet a specified criterion, a heart rate (HR) or a variability of the heart rate (HRV) can be computed from the cardiac activity signal at 803. The HR can be computed as a statistical index derived from the plurality of measurements of HR or CL, such as a mean, a median, or other central tendency measures of a plurality of measurements of HR or CL over a specified period of time. The HRV can be computed as a statistical measure such as a variance, standard deviation, or other statistics indicative of the variability of the plurality of HR measurements over a specified period of time. The computed HR or HRV can then be evaluated against respective threshold values, $HR_{TH1}$ or $HRV_{TH1}$, for AF onset event detection at 804. The threshold values can be determined using population-based statistics (such as derived from HR or HRV during AF across a number of patients) or using patient-specific statistics (such as derived from HR or HRV from the patient's historical AF episodes). In an example, the $HR_{TH1}$ and $HRV_{TH1}$ are selected such that the initial detection criterion at 804 is sensitive to presence of an AF episode. As an example, the $HR_{TH1}$ is approximately in the range of 120-150 beats per minute (bpm), and the $HRV_{TH1}$ is approximately in the range of 20-50 bpm.

If the sensed HR does not exceed the threshold value $HR_{TH1}$ and the sensed HRV does not exceed the threshold $HRV_{TH1}$, no initial AF onset event is deemed detected; and the AF onset detection process continues by receiving a cardiac activity signal at 801. However, if the sensed HR exceeds the threshold value $HR_{TH1}$ or the sensed HRV exceeds the threshold $HRV_{TH1}$, an AF onset event is deemed initially detected in the first stage detection, and a second stage AF onset event confirmation can by initiated by receiving a heart sound (HS) signal at 805. The HS signal can be sensed using a heart sound sensor such as an implantable, wearable, or otherwise ambulatory accelerometer or a microphone. At 806, the sensed HS signal can be processed and one or more HS components, including one or more of S1, S2, S3, or S4 heart sounds, can be detected. HS component strength ($\|HS\|$), such as intensity of S1 or S2 heart sounds, can be computed as the peak amplitude of the HS component determined from the time, frequency, or other transformed domain. Alternatively or additionally, a variability of a cardiac timing interval, such as a variability of a diastolic timing interval (DTIvar), can be determined using the sensed cardiac electrical activity and the detected HS component. The cardiac timing interval (CTI) represents the timing interval between two cardiac events. Examples of CTI can include systolic timing interval (STI), a diastolic timing interval (DTI), a pre-ejection period (PEP), or a composite measure using two or more different timing intervals selected from the STI, the DTI, the PEP, the CL, left ventricular ejection time (LVET) such as measured as a duration from the timing of S1 heart sound to a timing of S2 heart sound. Examples of the composite measures can include PEP/LVET ratio, STI/DTI ratio, STI/CL ratio, or DTI/CL ratio, among others.

The HS component strength ($\|HS\|$) or the variability of DTI (DTIvar) can then be compared to their respective threshold values $HS_{TH1}$ and $DTIvar_{TH1}$ at 807. If the $\|HS\|$ falls below the threshold value $HS_{TH1}$, or the DTIvar exceeds the threshold value $DTIvar_{TH1}$, a deterioration of cardiac hemodynamic status is indicated and the AF onset event can be confirmed. At 808, a declaration can be generated indicating a confirmed detection of an AF onset event. However, if at 807 the $\|HS\|$ exceeds the threshold value $HS_{TH1}$ and the DTIvar falls below the threshold value $DTIvar_{TH1}$, the patient cardiac hemodynamics is deemed not significantly impacted. As a result, the initially detected AF onset event is not confirmed by the second-stage process, and the AF onset detection process continues by receiving a cardiac activity signal at 801.

In some examples, the HS signal can be sensed prior to the initial detection of AF onset event or when patient is free of any arrhythmic event, and a reference or baseline level of $\|HS\|_0$ or $DTIvar_0$ can be established. The $\|HS\|$ and DTIvar computed following the initial AF onset detection at 806 can be compared to $\|HS\|_0$ or $DTIvar_0$ respectively at 807. An AF onset event is confirmed if a different between $\|HS\|$ and $\|HS\|_0$ falls below a specified threshold, or if an increase of DTIvar from the DTIvar$_0$ exceeds a specified threshold.

If an AF onset even is confirmed, an AF termination event detection process can be initiated to determine whether the AF episode sustains or terminates. Like the AF onset event detection, the AF termination event detection in the method 800 also involve a two-stage process, including the first stage of initial AF termination detection (811 through 814) based on one or more heart rate features, and the second stage of AF termination event confirmation (815 through 817) based on one or more heart sound features indicative of patient hemodynamic status. During the first stage of initial AF termination detection, HR and HRV computed at 813 from the cardiac activity signal can be compared to respective threshold HR$_{TH2}$ and HRV$_{TH2}$ at 814. The HR$_{TH2}$ can be greater than the HR$_{TH1}$, and the HRV$_{TH2}$ can be greater than the HRV$_{TH1}$. In an example, HR$_{TH2}$ is approximately in the range of 150-170 bpm, and HRV$_{TH2}$ is approximately in the range of 50-90 bpm. During the second stage of AF termination event confirmation, at 816 the HS component used for computing the $\|HS\|$, or the DTI index used for computing the DTIvar, can be different from those used in AF onset event detection. For example, a HS component or a DTI index having quick response and fast recovery following the AF termination can be selected for AF termination event detection. At 817 the $\|HS\|$ or the DTIvar are each compared to their respective threshold values HS$_{TH2}$ and DTIvar$_{TH2}$. If the $\|HS\|$ exceeds the threshold value HS$_{TH2}$, and the DTIvar falls below the threshold value DTIvar$_{TH2}$, a substantial hemodynamic recovery is indicated, and the AF termination event can be confirmed. A declaration can be generated indicating a confirmed detection of an AF termination event at 818. However, if at 817 the $\|HS\|$ or the DTIvar fail to meet their respective criterion, the patient cardiac hemodynamics is deemed not substantially recovered; and the initially detected AF termination event is not confirmed by the second-stage process. The AF termination detection process can be continued by receiving a cardiac activity signal at 811.

Figure 9:
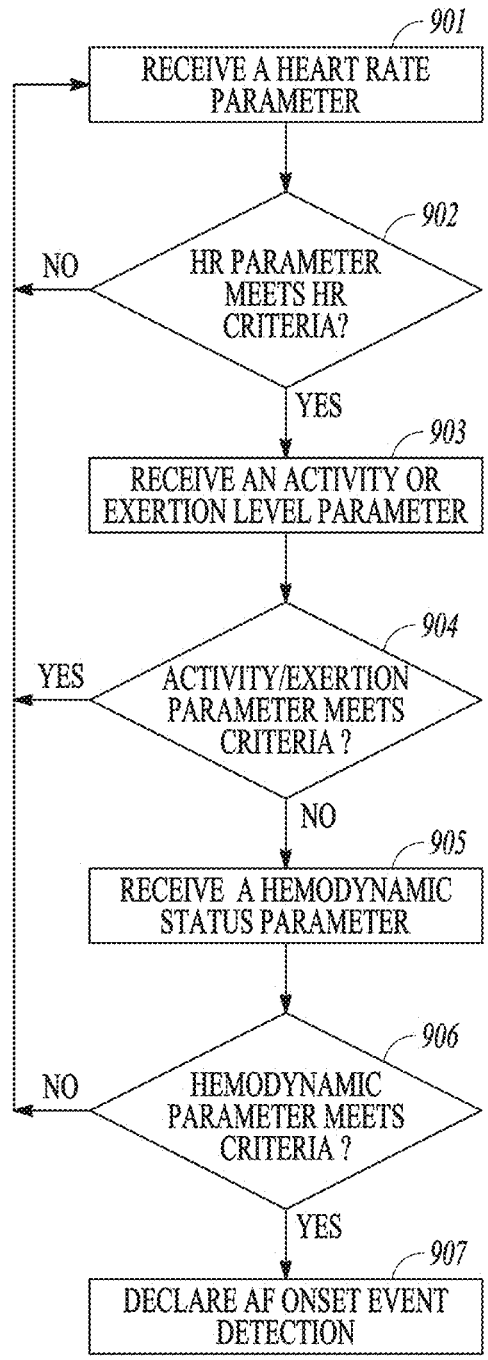
FIG. 9 illustrates an example of a method for detecting AF onset using heart rate, heart sounds, and activity level indicators.

FIG. 9 illustrates an example of a method 900 for detecting AF onset using heart rate, heart sounds, and activity level indicators. The method 900 can be an embodiment of the AF onset event detection portion of method 700 for detecting an AF onset event. The method 900 can be performed by the hemodynamic sensor-based AF event detection circuit 113.

The method 900 can detect the AF onset event using a three-stage process, with a first stage of initial AF onset detection (901 and 902) using one or more heart rate features, a second stage of confounding events elimination (903 and 904) using one or more activity or exertion level signals, and a third stage of AF onset event confirmation (905 and 906) using one or more heart sound features indicative of patient hemodynamic status.

One or more heart rate parameters can be sensed from a cardiac activity signal at 901. The heart rate parameters, such as HR or HRV as discussed in the method 800, can be compared to their respective threshold values to determine whether a specified criterion is met at 902. If the HR parameter meets the HR criteria at 902, an AF onset event is deemed initially detected in the first stage detection, and the second stage of confounding event elimination can by initiated by receiving an activity or exertion level parameter at 903. The activity or exertion level parameters can indicate vigorousness or duration of the patient's physical activity. In an example, the activity level parameter can be extracted from an acceleration signal acquired by an ambulatory accelerometer. The acceleration signal can be processed through a signal processing circuit to generate the activity or exertion level output of the patient. In another example, the activity level parameter can be extracted from a respiration signals such as a thoracic impedance signal indicative of ventilation level of the patient. The activity or exertion level parameter can include respiration rate signal, tidal volume signal, or minute ventilation signal, among others.

At 904, the activity or exertion level parameter can be evaluated against a specified criterion, such as a threshold value for the acceleration or the impedance value indicative of minute ventilation. If the activity or exertion level parameter meets the specified criteria at 904 such as a detected increase in acceleration or minute ventilation exceeding their respective threshold values, the increase in HR or HRV as detected in the initial detection stage is deemed caused by confounding factors of patient's physical activity or exertion. As such, the initially detected AF onset based on HR or HRV is not confirmed, and the process of detecting AF onset event can be continued by receiving heart rate parameters at 901. However, if there is no indication of substantial increase in acceleration or minute ventilation at 904, no confounding event is deemed present; and a third stage AF onset event confirmation can by initiated by receiving a hemodynamic parameter at 905. The hemodynamic parameters, such as HS component strength ($\|HS\|$) or the variability of a cardiac timing interval such as a variability of a diastolic timing interval (DTIvar), can be computed using at least a heart sound signal, as discussed in method 800. If the hemodynamic parameter meets a specified criterion, such as $\|HS\|$ falling below the threshold value HS$_{TH1}$, or the DTIvar exceeding the threshold value DTIvar$_{TH1}$, then an AF onset event is confirmed and declared at 907. Otherwise, no AF onset event detection is declared, and the process of detecting AF onset event can be continued by receiving heart rate parameters at 901.

The method 900 can be modified to detect an AF termination event using the three-stage process, with a first stage of initial AF termination detection using one or more heart rate features, a second stage of confounding events elimination using one or more activity or exertion level signals, and a third stage of AF termination event confirmation using one or more heart sound features indicative of patient hemodynamic status.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A medical system, comprising:
a heart rate sensor circuit configured to sense a heart rate output indicative of a heart rate of a patient;
a hemodynamic sensor circuit configured to sense a hemodynamic status output different from the heart rate output, the hemodynamic status output indicative of a hemodynamic status of the patient; and
an atrial fibrillation (AF) detector circuit communicatively coupled to the heart rate sensor circuit and the hemodynamic sensor circuit, the AF detector circuit including:
a detection criterion determination circuit configured to determine a first detection criterion and a different second detection criterion;
an AF event detector configured to detect an AF episode if at least one of the heart rate output or the hemodynamic status output satisfies the first detection criterion; and
an AF termination event detector configured to detect a termination of the detected AF episode if at least one of the heart rate output or the hemodynamic status output satisfies the second detection criterion;
wherein the first detection criterion is more sensitive to the AF episode than the second detection criterion, and the second detection criterion is more specific to the AF episode than the first detection criterion.

2. The system of claim 1, wherein the first detection criterion includes a heart rate criterion, and the second detection criterion includes a hemodynamic status criterion, and wherein:
the AF event detector is configured to detect the AF episode when the heart rate output meets the heart rate criterion; and
the AF termination event detector is configured to detect the termination of the detected AF episode when the hemodynamic status output meets the hemodynamic status criterion.

3. The system of claim 1, wherein:
the detection criterion determination circuit is configured to determine a first heart rate criterion, a different second heart rate criterion, a first hemodynamic status criterion, and a different second hemodynamic status criterion;
the AF event detector is configured to detect the AF episode when the heart rate output meets the first heart rate criterion and the hemodynamic status output meets the first hemodynamic status criterion, the first heart rate criterion is more sensitive to the AF episode than the second heart rate criterion, and the second heart rate criterion is more specific to the AF episode than the first heart rate criterion; and
the AF termination event detector is configured to detect the termination of the detected AF episode when the heart rate output meets the second heart rate criterion and the hemodynamic status output meets the second hemodynamic status criterion.

4. The system of claim 3, wherein the hemodynamic sensor circuit is configured to sense the hemodynamic status output in response to the heart rate output meeting the first or second heart rate criterion.

5. The system of claim 3, wherein:
the heart rate sensor circuit includes a cardiac activity sensor configured to sense a heart rate;
the detection criterion determination circuit is configured to automatically determine the first and second heart rate criteria including a first heart rate threshold value and a second heart rate threshold value higher than the first heart rate threshold value;
the AF event detector is configured to detect the AF episode when the sensed heart rate exceeds the first heart rate threshold value and the hemodynamic status output meets the first hemodynamic status criterion; and
the AF termination event detector is configured to detect the termination of the detected AF episode when the sensed heart rate falls below the second heart rate threshold value and the hemodynamic status output meets the second hemodynamic status criterion.

6. The system of claim 3, wherein:
the heart rate sensor circuit includes a cardiac activity sensor configured to sense a variability of heart rate;
the detection criterion determination circuit is configured to automatically determine the first and second heart rate criteria including a first variability threshold value and a second variability threshold value higher than the first heart rate threshold value;
the AF event detector is configured to detect the AF episode when the sensed variability of heart rate exceeds the first variability threshold value and the hemodynamic status output meets the first hemodynamic status criterion; and
the AF termination event detector is configured to detect the termination of the detected AF episode when the sensed variability of heart rate falls below the second variability threshold value and the hemodynamic status output meets the second hemodynamic status criterion.

7. The system of claim 1, wherein the hemodynamic sensor circuit includes:
a heart sound sensor configured to sense a heart sound (HS) signal;
a heart sound component detector circuit configured to detect, using the HS signal, one or more HS components including an S1, an S2 or an S3 heart sound; and
a hemodynamic parameter generator circuit configured to generate, using the detected one or more HS components, a HS metric indicative or correlative of hemodynamic status of the patient.

8. The system of claim 7, wherein the hemodynamic parameter generator circuit is configured to determine a variability of cardiac timing interval (CTIvar) using the detected one or more HS component.

9. The system of claim 8, wherein:
the hemodynamic parameter generator circuit is configured to determine the CTIvar including a variability of diastolic timing interval (DTIvar);
the detection criterion determination circuit is configured to automatically determine first ($DTIvar_{TH1}$) and second ($DTIvar_{TH2}$) threshold values of the DTIvar;
the AF event detector is configured to detect the AF episode when the heart rate output meets a first heart rate criterion and the DTIvar exceeds the $DTIvar_{TH1}$; and
the AF termination event detector is configured to detect the termination of the detected AF episode when the heart rate output meets a second heart rate criterion and the DTIvar falls below the $DTIvar_{TH2}$.

10. The system of claim 1, wherein the heart rate sensor circuit is further configured to calculate a signal quality index of the heart rate output, and wherein, in response to the calculated quality index failing to meet a specified quality criterion:
the AF event detector is configured to detect the AF episode when the hemodynamic status output meets a first hemodynamic status criterion; and
the AF termination event detector is configured to detect the termination of the detected AF episode when the hemodynamic status output meets a second hemodynamic status criterion.

11. The system of claim 1, further comprising a therapy delivery system configured to provide and deliver therapy to the patient in response to the detection of the AF episode, or to withhold the therapy to the patient in response to the detection of the termination of the detected AF episode.

12. The medical system of claim 1, further comprising an activity sensor circuit configured to sense an activity or exertion level output of the patient, wherein:
the first detection criterion includes a first heart rate criterion, a first hemodynamic status criterion, and a first activity or exertion level criterion;
the second detection criterion includes a different second heart rate criterion, a different second hemodynamic status criterion, and a different second activity or exertion criterion; the AF event detector is further configured to detect the AF episode when the heart rate output meets the first heart rate criterion, the hemodynamic status output meets the first hemodynamic status criterion, and the sensed activity or exertion level output meets the first activity or exertion criterion; and
the AF termination event detector is further configured to detect the termination of the detected AF episode when the heart rate output meets the second heart rate criterion, the hemodynamic status output meets the second hemodynamic status criterion, and the sensed activity or exertion level output meets the second activity or exertion criterion.

13. The system of claim 12, further comprising an ambulatory accelerometer communicatively coupled to the hemodynamic sensor circuit and the activity sensor circuit, the ambulatory accelerometer configured to sense an acceleration signal from the patient, wherein:
the activity sensor circuit is configured to process the sensed acceleration signal through a first signal processing circuit to generate the activity or exertion level output of the patient; and
the hemodynamic sensor circuit is configured to process the sensed acceleration signal through a second signal processing circuit different from the first signal processing circuit to generate a heart sound signal of the patient.

14. The system of claim 12, wherein the activity sensor circuit includes an impedance sensor configured to sense a thoracic impedance signal indicative of ventilation level of the patient.

15. A method for operating a medical system to detect an atrial fibrillation (AF) in a patient, comprising:
receiving a heart rate parameter sensed from the patient via a heart rate sensor;
receiving a hemodynamic status parameter sensed via a hemodynamic sensor, the hemodynamic status parameter different from the heart rate parameter from the patient;
determining or receiving, via the medical system, a first detection criterion and a different second detection criterion;
detecting, via the medical system, an AF episode if at least one of the heart rate output or the hemodynamic status output satisfies the first detection criterion;
detecting, via the medical system, a termination of the detected AF episode if at least one of the heart rate output or the hemodynamic status output satisfies the second detection criterion, the first detection criterion being more sensitive to the AF episode than the second detection criterion, and the second detection criterion being more specific to the AF episode than the first detection criterion.

16. The method of claim 15, wherein the first detection criterion includes a heart rate criterion, and the second detection criterion includes a hemodynamic status criterion, and wherein:

detecting the AF episode includes when the received heart rate parameter meets the heart rate criterion; and detecting the termination of the detected AF episode includes when the received hemodynamic status parameter meets the hemodynamic status criterion.

17. The method of claim 15, comprising determining or receiving a first heart rate criterion, a different second heart rate criterion, a first hemodynamic status criterion, and a different second hemodynamic status criterion, wherein:

detecting the AF episode includes when the received heart rate parameter meets the first heart rate criterion and the received hemodynamic status parameter meets the first hemodynamic status criterion; and detecting the termination of the detected AF episode includes when the heart rate parameter meets the second heart rate criterion and the hemodynamic status parameter meets the second hemodynamic status criterion, the first heart rate criterion being more sensitive to the AF episode than the second heart rate criterion, and the second heart rate criterion being more specific to the AF episode than the first heart rate criterion.

18. The method of claim 17, wherein:

receiving the heart rate parameter includes sensing at least one of a heart rate, a pulse rate, a variability of heart rate, or a variability of pulse rate;

determining or receiving the first and the different second heart rate criteria includes determining or receiving a first threshold value for the heart rate parameter and a second threshold value for the heart rate parameter, the second threshold value higher than the first threshold value;

detecting the AF episode includes when the sensed heart rate parameter exceeds the first threshold value for the heart rate parameter and the hemodynamic status output meets the first hemodynamic status criterion; and detecting the termination of the detected AF episode includes, in response to the detection of the AF onset, when the sensed heart rate parameter falls below the second threshold value for the heart rate parameter and the hemodynamic status output meets the second hemodynamic status criterion.

19. The method of claim 17, wherein:

receiving the hemodynamic status parameter includes sensing a heart sound signal using a heart sound sensor and computing from the sensed heart sound signal intensity of heart sound component ($\|HS\|$) including intensity of at least one of an S1 heart sound intensity or an S2 heart sound intensity;

determining or receiving the first and the different second hemodynamic status criteria includes automatically determining a first threshold value ($HS_{TH1}$) for the heart sound parameter and a second threshold value ($HS_{TH2}$) for the heart sound parameter;

detecting the AF episode includes when the heart rate output meets the first heart rate criterion and the computed $\|HS\|$ falls below the $HS_{TH1}$; and detecting the termination of the detected AF episode includes, in response to the detection of the AF onset, when the heart rate output meets the second heart rate criterion and the sensed $\|HS\|$ exceeds the $HS_{TH2}$.

20. The method of claim 17, wherein:

receiving the hemodynamic status parameter includes sensing a heart sound signal and computing from the sensed heart sound a variability of cardiac timing intervals including a variability of diastolic timing interval ($DTI_{var}$);

determining or receiving the first and the different second hemodynamic status criteria includes automatically determining a first threshold value ($DTIvar_{TH1}$) and a second threshold value ($DTIvar_{TH2}$) for the DTIvar;

detecting the AF episode includes when the heart rate output meets the first heart rate criterion and the computed DTIvar exceeds the $DTIvar_{TH1}$; and detecting the termination of the detected AF episode includes, in response to the detection of the AF episode, when the heart rate output meets the second heart rate criterion and the sensed DTIvar falls below the $DTIvar_{TH2}$.

* * * * *